United States Patent [19]

Ekman et al.

[11] Patent Number: 4,822,535
[45] Date of Patent: Apr. 18, 1989

[54] METHOD FOR PRODUCING SMALL, SPHERICAL POLYMER PARTICLES

[75] Inventors: Bo Ekman, Malmö ; Åke Lindahl, Skurup, both of Sweden

[73] Assignee: Norsk Hydro A.S., Oslo, Norway

[21] Appl. No.: 878,700

[22] Filed: Jun. 26, 1986

[30] Foreign Application Priority Data

Dec. 7, 1985 [SE] Sweden ................ 8503459

[51] Int. Cl.$^4$ .............................. B01J 19/06
[52] U.S. Cl. .......................... 264/4.3; 264/4;
264/4.1; 264/4.6; 264/4.7; 252/304; 252/310;
252/314; 427/213.3; 427/213.32; 427/213.33
[58] Field of Search ............... 264/4.3, 4.4, 4.6, 4.7,
264/4; 252/310, 314, 304; 427/213.3, 213.32,
213.36, 213.33

[56] References Cited

U.S. PATENT DOCUMENTS

| 3,155,590 | 11/1964 | Miller et al. | 264/4.3 |
| 3,205,175 | 9/1965 | Maierson | 264/4.3 |
| 3,634,394 | 1/1972 | Andraassen | 260/233 |
| 3,657,144 | 4/1972 | Yoshida | 264/4.3 |
| 3,897,414 | 7/1975 | Albertson | 260/211.5 R |
| 4,061,466 | 12/1977 | Ejohöln et al. | 23/230 B |
| 4,123,403 | 10/1978 | Warner et al. | 523/313 |
| 4,389,330 | 6/1983 | Tice et al. | 264/4.6 |
| 4,486,471 | 12/1984 | Somejima et al. | 427/213.3 |
| 4,540,602 | 9/1985 | Motoyama et al. | 427/213.36 |
| 4,606,940 | 8/1986 | Frank et al. | 427/213.3 |

FOREIGN PATENT DOCUMENTS

| 1162111 | 2/1984 | Canada | 427/213.3 |
| 0011837 | 6/1980 | European Pat. Off. . | |
| 1443359 | 10/1961 | Fed. Rep. of Germany . | |
| 56-89834 | 7/1981 | Japan | 264/4.1 |

Primary Examiner—Jan H. Silbaugh
Assistant Examiner—Hubert C. Lorin
Attorney, Agent, or Firm—Fred Philpitt

[57] ABSTRACT

A method of producing small spherical polymer particles from systems containing two liquid phases, the one phase of which contains one or more dissolved substances and is dispersed in the form of small droplets in the other phase to form an emulsion, whereafter the droplets are converted to a solid form. The liquid phases used are two mutually immiscible aqueous phases.

10 Claims, No Drawings

METHOD FOR PRODUCING SMALL, SPHERICAL POLYMER PARTICLES

The present invention relates to a method for producing small, spherical polymer particles from systems containing two liquid phases, the one phase of which contains one or more dissolved substances and is dispersed in the form of small droplets in the other phase to form an emulsion, whereafter the droplets are caused to solidify.

A large number of methods of the above mentioned type are known in the art. The known methods differ from one another mainly in applying different principles to convert the droplets to a solid (insoluble) form.

For example, DE-B No. 1 443 359 discloses a method in which the substance dissolved in the one phase comprises a polysaccharide and the droplets are converted to a solid form (gel form) by adding a cross-linking agent, thereby to form a cross-linked polysaccharide, which precipitates.

In another known method, which is disclosed in U.S. Pat. No. 3,634,394, the dissolved substance used is one, the solubility of which is dependent on pH, and precipitation (conversion of the droplets to solid form) is effected by changing the pH-value.

According to U.S. Pat. No. 4,061,466, which discloses another known method of the aforesaid kind, the dissloved substances constitute the monomers of a polymerisation system and the conversion of the droplets to a solid form is effected by polymerising the monomers to form an insoluble polymer.

In all of the known methods the one phase is an aqueous phase and the other phase comprises an organic solvent that is waterimmiscible, which results in certain drawbacks.

For example, the handling of this kind of organic solvents is not very desirable from the aspects of environmental care and the welfare of the working personnel involved. In many instances the use for which the particulate product produced is intended (e.g. therapeutical purposes) requires the product to be carefully purified in order to remove the last residues of solvent.

In other instances the produced particles, or biologically active molecules encapsulated in the particles or otherwise immobilized, may be damaged by the organic solvent.

Consequently, it is an object of this invention to provide a method of the aforesaid kind which is carried out with the use of a two-phase liquid system which is substantially less harmful than the two phase systems previously used and which enables immobilized substances sensitive to organic solvents to be produced without damaging said substances.

This object is achieved in accordance with the present invention by a method of the aforesaid kind which is characterized by using two mutually immiscible aqueous phases as the liquid phases.

Systems comprising two or more mutually immiscible aqueous phases have previously been used in the separation of macromolecular substances, vide for example EP-B No.1-0 011 837 and U.S. Pat. No. 3,897,414.

In aqueous two-phase systems of this kind, each phase normally has at least one polymer dissolved therein. Examples of such two-phase systems of polymeric aqueous solutions are: Dextran/water-soluble copolymer of sucrose and epichlorohydrin (Ficoll ®)/water, dextran/hydroxypropyl dextran/water, polyethylene glycol/dextran sulphate/water, dextran/polyethylene glycol/water, polypropylene glycol/methoxy polyethylene glycol/water, polypropylene glycol/polyethylene glycol/water, polypropylene glycol/polyvinyl alcohol/water, polypropylene glycol/polyvinylpyrrolidone/water, polypropylene glycol/hydroxypropyl dextran/water, polypropylene glycol/dextran/water, polyethylene glycol/polyvinyl alcohol/water, polyethylene glycol/polyvinylpyrrolidone/water, polyethylene glycol/Ficoll ®/water, polyethylene glycol/soluble starch/water, polyethylene glycol/glycogen/water, polyvinyl alcohol/methyl cellulose/water, polyvinyl alcohol/hydroxypropyl dextran/water, polyvinyl alcohol/dextran/water, polyvinylpyrrolidone/methylcellulose/water, polyvinylpyrrolidone/dextran/water, methylcellulose/hydroxypropyl dextran/water, methylcellulose/dextran/water, and ethylhydroxyethyl cellulose/dextran/water.

Other groups of aqueous two-phase liquid systems are: At least one polymer/at least one salt/water, and at least one polymer/at least one water-miscible organic solvent/water. The salt may be an inorganic or organic salt, which is soluble in water, for example a sulphate, a phosphate or a chloride, for example magnesium sulphate, potassium phosphate or sodium chloride. Examples of water-soluble organic solvents which can be used in aqueous two-phase systems in conjunction with the method according to the invention are propyl alcohol, glycerol, ethanol, acetone, and isopropyl alcohol.

It is possible in some of the above systems to convert the polymeric component of one phase to a solid form. When using other systems, there can be used a third polymeric component which dissolves in one of the two phases and can then be solidified.

In those instances where a third polymeric component is present, there is chosen a two-phase system in which the major part of this component is partitioned in the one phase. In addition, the polymer in the phase which incorporates the major part of said component is preferably physiologically innocuous when the end product is to be used for therapeutical purposes, since the aforesaid polymer will be present in the end product.

The conversion of the droplets with the substance dissolved therein to a solid state in the method according to the invention can be effected with both physical and chemical methods, the method to be chosen being dependent on the nature of dissolved substance chosen.

According to one embodiment of the method according to the invention a substance which is moderately soluble in water is used as a dissolved substance in the phase to be dispersed to the form of small droplets, and the droplets are solidified by removing water therefrom.

Examples of substances which can be used in this respect are starch, agar, gelatin, pectin, collagen, carrageenan and fibrin.

Water can be removed from the dispersed phase by disturbing the equilibrium of the two-phase system, wherewith the system strives to achieve a new equilibrium, by transferring water from the dispersed phase to the continuous phase, which results in the precipitation of the substance or substances of moderate solubility in water present in the dispersed phase when the solubility of the substance or substances is exceeded.

One way to achieve removal of water from the dispersed phase comprises the application of methods such as evaporation, dialysis or ultrafiltration.

Evaporation increases the content of osmotically active substances in the continuous phase ("solvent evaporation"). The evaporation process can be effected by heating the system while stirring the same. If desired, the process can also be carried out at reduced pressure.

When dialysis is utilized a concentration of osmotically active components is also taking place. To this end there is used a membrane which is permeable solely to water, which also allows the water content of the dispersed phase to be accurately controlled.

The same result is achieved with ultrafiltration.

Another way to achieve removal of water from the dispersed phase comprises the addition of substances to the continuous phase, which results in the transfer of water to the dispersed phase, e.g. by osmosis.

For example, when polyethylene glycol is the polymer in the continuous phase (the outer phase) further polyethylene glycol is primarily added thereto, this addition suitably being in the form of an aqueous solution having a higher polyethylene glycol content than the solution originally used for this phase. The addition, however, may also comprise an aqueous solution of sodium chloride or other osmosis-elevating salts of magnesium, zinc, and other metals.

Subsequent to the formation of the particles in gel form, further water can be extracted from the gel particles by adding a water-miscible solvent, such as ethanol and acetone.

The two-phase system may also be prepared by dissolving each of the two polymers which are to enter their own particular phase separately in water, the concentration of the polymers in respective solutions being chosen so that when the solutions are stirred together to form an emulsion water will pass from the inner phase (the dispersed phase) to the outer phase.

When practising this embodiment, polyethylene glycol is preferably used as the polymer in the continuous phase, the average molecular weight ($\overline{M}_w$) of the polyethylene glycol normally being chosen from the range 100–2,000,000 Daltons.

The concentration chosen for the polymers in the two phases is governed partly by the desire to form a two-phase liquid system and partly by the desire to obtain a high polymer concentration in the dispersed phase, so that only a small amount of water need be removed in order for the polymer particles to precipitate. Suitable concentrations can be most readily established in each particular case by simple experimentation, where both polymers are dissolved in water.

In this respect, it is beneficial to establish a suitable (high) concentration for the polymer which is to form the inner phase and to vary the concentraiton of the other polymer for achieving a two-phase system.

Generally speaking, when proceeding in accordance with the invention, the amount of polymer incorporated in the continuous phase shall be sufficiently high to provide a clearly defined two-phase system, and no advantage is gained by adding polymer over and above this amount.

According to another embodiment of the method of the invention, methyl cellulose or one or more proteins is used as a substance dissolved in the dispersed phase, and the conversion of the droplets to solid form is achieved by heating the system.

This embodiment is based on the fact that certain polymers phase-separate at temperatures above the theta-temperature. In this embodiment the polymer solution is dehydrated during the phase separation and the dispersed phase is precipitated as solid particles.

When the polymer in the dispersed phase is methylcellulose, the polymer in the continuous phase may be, for example, polyvinylpyrrolidone, polyvinyl alcohol, hydroxypropyl dextran or dextran.

The polymers are preferably dissolved separately and the separate solutions then mixed together in a manner known per se while stirring, to form a dispersion. The temperature of the dispersion is then gradually raised until particles have formed or until the temperature approaches boiling point, e.g. to 95° C. The formed beads are separated by centrifugation or filtration, which is preferably carried out in a warm environment to prevent re-dissolution of the methylcellulose, whereafter the particles are dried.

Suitable concentrations of the polymers in the two phases can be established by simple experimentation in the same manner as that described with the embodiment in which the dispersed phase was converted to solid form by removing water from said phase.

When the polymer used in the dispersed phase comprises one or more proteins, it is assumed that the system is heated in a manner to denature the proteins so that they solidify. Naturally, this method is not applied when wishing to retain the protein in the state of not being denatured.

The polymer used in the continuous phase is primarily polyethylene glycol, although other polymers, such as dextran and polyvinyl alcohol, can also be contemplated. The average molecular weight ($M_w$) of the polyethylene glycol used is normally chosen from the aforesaid range of 100–2 000 000 Daltons.

To facilitate the formation of a two-phase system, it may be necessary to use the protein together with another polymer, such as dextran, for example, with an average molecular weight of 40 000–2 000 000 Daltons. Methylcellulose is another polymer which can be used in this context.

The formation and isolation of the particles is effected in a way analogously with that described above with reference to methylcellulose.

According to a third embodiment of the method according to the invention a polymer whose solubility in water is highly dependent on temperature is used as a dissolved substance, and conversion of the droplets to solid form is effected by cooling the system.

Examples of suitable polymers in the dispersed phase in this respect are starch, agar, gelatin, pectin, and carrageenan. The starch can be of various types and starch derivatives can also be used, provided that they are capable of forming gels in water.

The polymer is dissolved in water at high temperature, preferably at the highest possible temperature with regard to respective polymers, and to a concentration as close as possible to the solubility limit of the polymer.

Generally speaking, the polymer used in the continuous phase may be any polymer capable of forming a two-phase system with the polymer in the inner-phase, provided that it does not behave in the same manner as this latter polymer when subjected to changes in temperature. When the polymer in the dispersed phase is starch, the polymer in the continuous phase is primarily polyethylene glycol having the aforesaid average molecular weight.

The polymer intended for the continuous phase is dissolved separately and the solution is brought to a temperature which will prevent the solution intended to form the dispersed phase from cooling too rapidly when stirred together with the first mentioned solution to form a two-phase system in the form of a dispersion. The system is then allowed to cool, wherewith the polymer in the dispersed phase gradually precipitates. When the mixture has reached room temperature, the particles are isolated, e.g. by filtration. Optionally, a dehydrating agent, such as ethanol or acetone, can be added to the cooling mixture prior to filtration.

According to a fourth embodiment of the method according to the invention a polymer which possesses hydroxyl groups and/ or amino groups or groups containing the structure $CH_2=CH-$ is used as a dissolved substance and the droplets are solidified by a cross-linking reaction.

In this regard, the hydroxyl-group containing polymers are primarily polysaccharides. The compounds can be cross-linked with the aid of bifunctional cross-linking agents, such as a bifunctional glycerol derivative of the kind dichlorohydrin or dibromohydrin or corresponding epoxide compounds obtainable by splitting off hydrogen halides, i.e. epichlorohydrin or epibromohydrin, or a diepoxide, such as 1,2-3,4-diepoxybutane for example.

For example, when the polymer in the dispersed phase is dextran sulphate, the outer phase may comprise an aqueous solution of a salt which forms a two-phase system with dextran sulphate. Cross-linking can be effected by adding an ethanol solution of epichlorohydrin.

Examples of polymer substances containing amino groups for use with this embodiment of the invention are polypeptides, including proteins. These substances can be cross-linked with the aid of methods known per se, for example with glutaric aldehyde or formaldehyde as the cross-linking agent.

In this case, the polymer in the continuous phase is preferably polyethylene glycol.

The polymer for the continuous phase and the polypeptide are dissolved separately in water, preferably at room temperature. The solutions are then brought together while stirring to form a two-phase system, in which the solution containing the polypeptide forms a dispersed phase. When the two-phase system has developed, an aqueous solution of the cross-linking agent is added with continued stirring. The cross-linking reaction is normally effected at room temperature. It is also possible to work at a slightly elevated temperature, although when the system contains a biologically active substance whose activity is to be retained, the system shall not be heated to a temperature of such magnitude as to destroy this activity.

The resultant solid product is isolated by conventional methods, such as filtration, and then dried.

Examples of polymers exhibiting groups which contain the structure $CH_2=CH-$ for use in this embodiment of the invention include acryl-substituted polysaccharides, such as acryldextran, acrylstarch, etc.

The polymer used in the continuous phase in this respect is preferably polyethylene glycol (average molecular weights as with the earlier mentioned embodiments where this polymer is used), although other polymers may also be contemplated for this use, for example methylcellulose in case of acryldextran in the dispersed phase.

The polymers are dissolved separately in water and the solution for the dispersed phase is stirred into the outer solution, suitably at room temperature, to form a dispersion. Subsequent to producing the two-phase system, there is added an aqueous solution of a substance which catalyses the cross-linking reaction, such as ammonium peroxosulphate and N,N,N',N'-tetramethylethylenediamine for example. Subsequent to the termination of this reaction, the resultant particles are isolated in a conventional manner, e.g. by centrifugation or filtration.

According to a fifth embodiment of the method according to the invention, a polymer whose solubility is greatly dependent on pH is used as a dissolved substance, and the droplets are converted to a solid form by changing the pH of the dispersed phase.

Examples of polymers whose solubility in water is greatly dependent on pH, and which can therefore be used with this embodiment, include alginic acid, carboxymethylcellulose, celluloseacetatephthalate, pectin and starch.

In this embodiment the polymer used in the continuous phase is preferably polyethylene glycol (average molecular weight as above) to which sodium chloride is added. Other polymers can also be used in this conext. For example, when the polymer in the dispersed phase is carboxymethylcellulose, the continuous phase may comprise polypropylene glycol, methoxypolyethylene glycol, polyvinyl alcohol, polyvinylpyrrolidone, methylcellulose, ethylhydroxyethylcellulose, or hydropropyl dextran, sodium chloride being added in all cases.

When preparing the polymer solution for the dispersed phase, it may be necessary to add an alkaline substance, preferably sodium hydroxide, in order to provide a pH at which the polymer will dissolve.

The polymer solution for the dispersed phase is made as highly concentrated as possible. In this respect, the upper limit of the concentration may be decided by the viscosity of the solution, in addition to the solubility of the polymer.

The aqueous solutions for the two phases are preferably prepared separately and then brought together, the solution for the dispersed phase preferably being added to the other solution while stirring to form a dispersion.

When the two-phase system has been formed there is added dropwise a dilute acid, preferably an inorganic acid such as hydrochloric acid, while continuing to stir the system until the dispersed phase has solidified. All operations are preferably carried out at room temperature.

The resultant particles are isolated in a conventional manner, for example by centrifugation or filtration.

According to a sixth embodiment of the method according to the invention a polymer which forms a sparingly soluble salt with a preferably non-toxic counter-ion is used as a dissolved substance, and the droplets are converted to a solid form by adding such a counter-ion.

Examples of polymers which can be used with this embodiment of the method according to the invention include electrically charged polymers, such as sodium alginate, capable of forming sparingly soluble salts with one or more of the ions $Ca^{2+}$, $K^+$ etc. Examples of other polymers which can be used include pectin and carrageenan, which form a gel with one or more of the ions $K^+$, $Ca^{2+}$, $Cs^+$ and $Rb^+$.

The polymer primarily used in the continuous phase is polyethylene glycol (average molecular weight as above).

The aqueous solutions for respective phases are preferably prepared separately and then brought together, the solution for the dispersed phase preferably being added to the other solution while stirring to form a dispersion.

Subsequent to the formation of the two-phase system there is added thereto an aqueous solution of a water-soluble salt containing the ion which forms a sparingly soluble salt with the polymer in the dispersed phase. When the ion in question is a metal ion, the salt used is normally a chloride, provided that it is soluble in water.

The particles formed are isolated in a conventional manner, for example by centrifugation or filtration.

All operations are advantageously carried out at room temperature.

According to a seventh embodiment of the method according to the invention at least one substance which constitutes a component in a system of at least two substances which react with each other to form a conjugate or complex which will not dissolve in an aqueous medium is used as a dissolved substance, and the droplets are solidified with the aid of the remaining components present in said system.

Systems which may be contemplated in this context are, for example, antigen-antibodies, heparin-protamines, proteinsnegatively charged hydrocolloids, etc. In the case of low contents, there is preferably added an auxiliary polymer, such as dextran, to facilitate the formation of the two-phase system.

The polymer primarily contemplated for use in the continuous phase is polyethylene glycol (average molecular weight as above).

A solution of one of the components of the aforesaid system and a solution of the polymer for the continuous phase are prepared separately whereafter the two solutions are brought together, the solution for the dispersed phase preferably being added to the other solution while stirring to form a dispersion.

Subsequent to forming the dispersion there is added thereto an aqueous solution of the remaining components of the system.

The resultant particles are isolated in a conventional manner, for example by centrifugation or filtration.

All these operations are advantageously carried out at room temperatures.

According to an eighth embodiment of the method according to the invention, the droplets are converted to solid form by splitting-off hydrophilic substituents from and/or introducing hydrophobic substituents into the dissolved substance.

The structural change to the polymer in the dispersed phase can be effected by chemical or enzymatical methods.

In principle, this embodiment is carried out by dissolving the polymers of the two phases separately in water and then bringing the two solutions together, while stirring to form a dispersion. When the dispersion has been formed there is added thereto an aqueous solution of the chemical reagent or the enzyme which produces the structural change of the polymer in the dispersed phase, to form a water-insoluble substance. The resultant particulate solid is isolated in a conventional manner, for example by centrifugation or filtration.

The particle size of the solid particles obtained can be controlled in all of the aforesaid embodiments in a manner known per se, for example by stirring with varying intensities or by selecting suitable viscosities for the various phases. In the case of the system polyethylene glycol-starch the particle size can also be regulated by selection of the molecular weight of the polyethylene glycol, a polyethylene glycol of higher molecular weight providing larger particles.

The particles produced when practising the invention are mainly amorphous. (They contain in general more than 80% amorphous material).

In accordance with a further aspect of the invention, one or more substances, which are inert during the process of converting the droplets to a solid form and which preferably are macromolecular substances, may be included as dissolved substances in the dispersed phase and be enclosed or entrapped in the particles as they form.

In addition, also whole (living) cells, cell organelles, solid particles or small oil droplets can be encapsulated when practising the invention.

With this encapsulation of substances in particle form or in the form of an emulsion droplet, the particle or emulsion droplet is provided with a casing or shell of the polymer which, in accordance with the invention, is intended to be converted to a solid form (to a particle). The substance to be encapsulated in the particle is then dispersed either in a solid form or in the form of oil droplets in a solution of said polymer. Particles, with encapsulated component in solid form or in oil form, are then formed with the aid of one of the aforedescribed embodiments of the method according to the invention.

In addition, low molecular substances can be incorporated in the particles by chemically binding the component to be incorporated to the particle-forming polymer by covalent or ion bonds. It is also possible to bind smaller molecules to a water-soluble ion-exchange substance, whereafter the ion-exchange substance is incorporated physically in the particles.

Low molecular substances which can be incorporated in this way may have the form of, for example, medicaments, vaccines or insecticides. When encapsulating heat-sensitive substances, the substances should not, of course, be heated to harmful temperatures.

The invention will now be illustrated in more detail with the aid of a number of non-limitative working examples.

EXAMPLE 1

Preparation of spherical particles of starch 2 g potato starch were dissolved in 45 ml of water at 90° C., to form a first solution which was brought to room temperature. A second solution was prepared by dissolving 5 g of polyethylene glycol ($\overline{M}_w=6000$). The starch solution was then added to the polyethylene glycol solution at room temperature, while stirring to form an emulsion. When the two-phase system had formed, the osmolarity of the outer phase was increased by adding a solution of 10 g of polyethylene glycol in 40 ml water.

10 minutes after completing the addition of polyethylene glycol solution the resultant starch particles were filtered off and then slurried in 100 ml of acetone. The slurry was then filtered and the starch particles were laid out to dry in air. Yield 90%.

EXAMPLE 2

Preparation of spherical particles of methylcellulose

A first solution was prepared from 3 g of methyl cellulose (MC 4000 from Dow Chemical Co., USA) in 47 ml of water, and a second solution from 3 g of dextran ($\overline{M}_w$=70 000) in 47 ml of water at room temperature. The solution of methylcellulose was added to the dextran solution while stirring, to form an emulsion. When the two-phase system (with the methylcellulose solution as the inner phase) had formed, the temperature of the system was gradually raised to 60° C. over a period of 30 minutes. When this temperature was reached, the inner phase had converted to a particle form. 100 ml of water heated to a temperature of 60° C. were then added, whereafter the particles were filtered-off and dried in a drying cabinet at 60° C.

The yield was 85%.

EXAMPLE 3

The preparation of spherical particles of albumin

A first solution was prepared from 1 g of bovine serum albumin and 5 ml of water, and a second solution from 9 g of polyethylene glycol ($\overline{M}_w$=6000) and 20 ml of water at room temperature.

In a manner analogous with Example 2 the two solutions were brought together and particles formed by heating, whereafter the particles were isolated and dried.

As an alternative, particles can be produced without heating, if the dispersed phase is dehydrated with a watermiscible solvent, such as ethanol, acetone, etc.

EXAMPLE 4

The preparation of spherical particles of starch 5 g potato starch were dissolved in 95 ml of water at about 90° C. A second solution was prepared from 3 g of polyethylene glycol ($\overline{M}_w$=6000) and 47 ml of water. This solution was heated to about 70° C., whereafter the warm starch solution was added while stirring, to form an emulsion. When the two-phase system had formed (with the starch solution as the inner phase) the mixture was allowed to cool to room temperature under continued stirring, wherewith the inner phase was converted to gel particles. The particles were filtered off at room temperature and slurried in 100 ml of ethanol, whereafter the particles were again filtered off and laid to dry in air. The yield was 90%.

EXAMPLE 5

The preparation of spherical particles of carrageenan

A first solution was prepared from 2 g of carrageenan and 48 ml of water at about 65° C., and a second solution was prepared from 5 g of polyethylene glycol ($\overline{M}_w$=6000) and 45 ml of water. The polyethylene glycol solution was heated to about 60° C., whereafter the warm carrageenan solution was added while stirring, to form an emulsion. When the two-phase system (with the carrageenan solution as the inner phase) had formed, the mixture was allowed to cool to room temperature under continued stirring, wherewith the inner phase was converted to particle form. The particles were isolated in a corresponding manner to the starch particles of Example 4. The yield was 95%.

EXAMPLE 6

The preparation of spherical particles of cross-linked dextran

A first solution was prepared from 5 g of acryldextran ($\overline{M}_w$=40 000) and 45 ml of water. (Acryldextran is dextran chains which have been derivated with acryl groups, these latter being capable of reacting to form cross-links, therewith to provide an insoluble gel. For the preparation of acryl dextran see P. Edman et al. J. Pharm.Sci. 69 No. 7 1980). A second solution was prepared from 7 g of polyethylene glycol ($\overline{M}_w$=6000) and 45 ml of water. The acryl dextran solution was added to the polyethylene glycol solution at room temperature while stirring, to form a dispersion. When the two-phase system had been formed (with the acryl dextran solution as the inner phase), there were added a few droplets of an aqueous solution comprising 500 mg of ammoniumperoxodisulphate per ml of water. A few drops of N,N,N',N'-tetramethylethylenediamine were then added. This catalyst system initiated the cross-linking reaction, which was allowed to proceed for 15 minutes. The particles were filtered off upon completion of the reaction. The yield was 95%.

EXAMPLE 7

The preparation of spherical particles of alginic acid

A first solution was prepared by dissolving 2 g of sodium alginate in 45 ml of water, and a second solution by dissolving 2 g of sodium chloride and 5 g of polyethylene glycol ($\overline{M}_w$=6000) in 43 ml of water. The alginate solution was added to the polyethylene glycol solution at room temperature while stirring, to form an emulsion. When the two-phase system had formed (with the alginate solution as the inner phase), 5 ml of 1N HCl were added dropwise, wherewith the inner phase was converted to particle form. The resultant particles of alginic acid were isolated by filtration. Drying was carried out in a corresponding manner to Example 4, by slurrying in ethanol, filtration and air-drying.

The yield was 85%.

EXAMPLE 8

The preparation of spherical particles of calcium alginate

A first solution was prepared by dissolving 2 g of sodium alginate in 48 ml of water, and a second solution by dissolving 2 g of sodium chloride and 5 g of polyethylene glycol ($\overline{M}_w$=6000) in 43 ml of water. The alginate solution was added to the polyethylene glycol solution at room temperature while stirring, to form an emulsion. When the two-phase system had been formed (with the alginate solution as the inner phase) 5 ml of 1 M CaCl$_2$ were added dropwise to the system, wherewith the inner phase was converted to particle form. The thus obtained particles of calcium alginate were isolated by filtration. The particles were dried in a drying cabinet at 35° C.

The yield was 85%.

EXAMPLE 9

The preparation of spherical particels of pectin gel

A first solution was prepared by dissolving 2.5 g pectin, lightly esterified with methoxy groups, in 47.5 ml of water, and a second solution by dissolving 5.0 g of polyethylene glycol ($\overline{M}_w$=6000) and 2 g of sodium chloride in 43.0 ml of water. The pectin solution was added to the polyethylene glycol solution at room temperature while stirring, to form an emulsion. When the two-phase system had been formed (with the pectin solution as the inner phase) 5 ml of 1 M CaCl$_2$ were added dropwise, wherewith the inner phase was converted to a particle form. The thus obtained particles of pectin gel were isolated by filtration and dried in a drying cabinet at 35° C.

The yield was 85%.

EXAMPLE 10

The preparation of spherical particles of fibrin

A first solution was prepared by dissolving 0.2 g of fibrinogen in 20 ml of physiological saline, and a second solution was prepared by dissolving 1 g of polyethylene glycol ($\overline{M}_w = 6000$) in 20 ml of water. The fibrinogen solution was added to the polyethylene glycol solution while stirring, to form a dispersion. When the two-phase system had been formed (with the fibrinogen solution as the inner phase) there were added a few drops of an aqueous solution of thrombin, wherewith the inner phase was converted to a fibrin gel. The thus obtained particles were dehydrated with ethanol and isolated by filtration or centrifugation.

We claim:

1. A method of producing small spherical polymer particles from a system containing two mutually immiscible aqueous liquid phases, the one phase of which contains one or more dissolved polymer substances and is dispersed in the form of small droplets in the other phase to form an emulsion, whereafter the droplets are caused to solidify to form said particles, and wherein said two mutually immiscible aqueous liquid phases both contain dissolved substances which will cause the formation of dispersed droplets when the two phases are brought together.

2. A method according to claim 1, wherein a substance which has a moderate solubility in water is used as said dissolved substance in said one phase, and said droplets are caused to solidify by removing water.

3. A method according to claim 1, wherein methylcellulose or one or more proteins is used as said dissolved substance in said one phase, and the conversion of said droplets to a solid form is effected by heating the system.

4. A method according to claim 1, wherein a polymer whose solubility in water is greatly dependent on temperature is used as said dissolved substance in said one phase, and the conversion of said droplets to a solid form is effected by cooling the system.

5. A method acording to claim 1, wherein a polymer exhibiting hydroxyl groups, amino groups, or hydroxyl and amino groups, or groups containing the structure $CH_2=CH-$, is used as said dissolved substance in said one phase, and the conversion of said droplets to a solid form is effected by means of a cross-linking reaction.

6. A method according to claim 1, wherein a polymer whose solubility is greatly dependent on pH is used as said dissolved substance in said one phase, and the conversion of said droplets to a solid form is effected by altering the pH-value of the dispersed phase.

7. A method according to claim 1, wherein a polymer which forms a sparingly soluble salt with a counter-ion is used as said dissolved substance in said one phase, and the conversion of said droplets to a solid form is effected by adding said counter-ion to said system.

8. A method according to claim 1, wherein at least one substance which constitutes a component in a system comprising at least two substances which react with one another to form a conjugate or complex which is insoluble in an aqueous medium is used as said dissolved substance in said one phase, and the conversion of said droplets to a solid form is effected with the aid of remaining components in said system.

9. A method according to claim 1, wherein the conversion of the droplets to a solid form is effected by at least one of splitting-off hydrophilic substituents from the dissolved substance, introducing hydrophobic substituents to the dissolved substance, or both, in said one phase.

10. A method according to claim 1, wherein one or more substances which are inert during conversion of said droplet to a solid form, are included as dissolved substances in the dispersed phase, and are subsequently enclosed or entrapped in the particles during the formation thereof, or whole cells, cell organs, solid particles or small oil droplets are dispersed in the dispersed phase and are encapsulated in the particles as they are formed.

* * * * *